US010902382B2

(12) United States Patent
Callahan et al.

(10) Patent No.: US 10,902,382 B2
(45) Date of Patent: Jan. 26, 2021

(54) METHODS FOR REMOTELY ACCESSING ELECTRONIC MEDICAL RECORDS WITHOUT HAVING PRIOR AUTHORIZATION

(71) Applicant: Hipaat, Inc., Mississauga (CA)

(72) Inventors: Terrance Callahan, Shelbourne (CA); Roman Bialach, Binbrook (CA); Chun Man Yeung, Scarborough (CA)

(73) Assignee: Hipaat, Inc., Mississauga (CA)

( * ) Notice: Subject to any disclaimer, the term of this patent is extended or adjusted under 35 U.S.C. 154(b) by 681 days.

(21) Appl. No.: 14/481,294

(22) Filed: Sep. 9, 2014

(65) Prior Publication Data

US 2014/0379380 A1 Dec. 25, 2014

Related U.S. Application Data

(63) Continuation of application No. 14/130,811, filed as application No. PCT/CA2012/000648 on Jul. 5, 2012, now abandoned.

(Continued)

(51) Int. Cl.
*G16H 10/60* (2018.01)
*G06Q 10/10* (2012.01)
*G06Q 50/24* (2012.01)

(52) U.S. Cl.
CPC ........... *G06Q 10/103* (2013.01); *G06Q 50/24* (2013.01); *G16H 10/60* (2018.01)

(58) Field of Classification Search
USPC ........................................................ 705/2, 3
See application file for complete search history.

(56) References Cited

U.S. PATENT DOCUMENTS

| 6,073,106 A | 6/2000 | Rozen et al. |
| 7,181,017 B1 | 2/2007 | Nagel et al. |

(Continued)

OTHER PUBLICATIONS

Healthcare Information and Management Systems Society (HIMSS), HIMSS Healthcare Information Exchange National / International Technology Guide White Paper, Apr. 2009.*

(Continued)

*Primary Examiner* — Aryan E Weisenfeld
*Assistant Examiner* — Joshua B Blanchette
(74) *Attorney, Agent, or Firm* — Neal, Gerber & Eisenberg LLP

(57) ABSTRACT

Methods are provided for allowing patients, health care practitioners and other service providers to have remote access to electronic medical records of a patient stored on a first computer network by the remote user requesting access to the electronic medical record from a second computer network and providing a first and second piece of patient derived information to the second computer network; the second computer network transferring the first and second piece of patient derived information to a third computer network; the third computer network authorizing the remote user through the first and second piece of patient derived information and dependent on a patient specific authorization protocol; the third computer network confirming a patient specific consent protocol; and the third computer network disclosing the electronic medical record to the remote user dependent upon an authorization and a confirmation received from the third computer network.

10 Claims, 7 Drawing Sheets

Related U.S. Application Data

(60) Provisional application No. 61/504,526, filed on Jul. 5, 2011.

(56) References Cited

U.S. PATENT DOCUMENTS

| | | | |
|---|---|---|---|
| 2006/0010015 A1 | 1/2006 | Thomas et al. | |
| 2008/0046292 A1* | 2/2008 | Myers | G16H 10/60 |
| | | | 705/3 |
| 2009/0012817 A1* | 1/2009 | Squires | G06Q 10/10 |
| | | | 705/3 |
| 2009/0144087 A1* | 6/2009 | Kelsch | G06Q 50/22 |
| | | | 705/3 |
| 2010/0082369 A1* | 4/2010 | Prenelus | G06Q 50/24 |
| | | | 705/3 |
| 2010/0241595 A1* | 9/2010 | Felsher | G06Q 30/0283 |
| | | | 705/400 |
| 2011/0022414 A1 | 1/2011 | Ge et al. | |
| 2011/0288877 A1* | 11/2011 | Ofek | G16H 10/60 |
| | | | 705/2 |

OTHER PUBLICATIONS

Healthcare Information and Management Systems Society (HIMSS), HIMSS Guide to Participating in a Health Information Exchange, Nov. 2009.*

Naikuo Yang et al. "A Purpose-Based Access Control Model." Journal of Information Assurance and Security 1 (2008) 51-58 (Year: 2008).*

Jing Jin et al. "Patient-centric Authorization Framework for Sharing Electronic Health Records." Proceedings of the 14th ACM symposium on Access control models and technologies Jun. 2009 pp. 125-134 (Year: 2009).*

* cited by examiner

400

This Service allows Healthcare Providers worldwide to access a patient's healthcare information.

To begin, please choose the country in which you are located.

| Canada▼ | United States | Mexico | Select Other▼ |

--Select One--
Alberta
British Columbia
Manitoba
New Brunswick
Newfoundland and Labrador
Northwest Territories
Nova Scotia
Nunavut
Ontario
Prince Edward Island
Quebec
Saskatchewan
Yukon

Please enter the patient's Identification Number. This information can be found on the back of the patient's Healthcare Access card.

If the patient is conscious, then please ask the patient for their Pass-Phrase.

Patient's ID [553-22-9402] ⟵ 601
Pass-Phrase [hipaat1234] ⟵ 602

[ Back ] [ Next ] [ I Do Not Have the Pass-Phrase ]

Please verify the patient's identity.

*Patient's ID*     553-22-9402
*Full Name*     Graves, Peter P.
*Address*     Hamilton
*Date of Birth*     1965-10-26

You must select a reason to Continue.

By doing so you agree not to re-disclose any healthcare information obtained.

| Examination, assessment, observation or detention under the Mental Health Act ▼ |

Enter additional details below.

[                                                                  ]

[ Back ] [ Continue ] [ Cancel ]

FIG.7

METHODS FOR REMOTELY ACCESSING ELECTRONIC MEDICAL RECORDS WITHOUT HAVING PRIOR AUTHORIZATION

FIELD OF INVENTION

The present invention relates to accessing personal health information (PHI), electronic health records (EHR) or electronic medical records (EMR) and more specifically to methods and system for remotely accessing a patient's electronic personal health information without prior authorization and/or authentication.

BACKGROUND TO THE INVENTION

The move to paperless electronic health records and the on-line access to health records for personal health information (PHI) is starting to gain momentum.

In the current environment, however, access to PHI, particularly in a digital or electronic format (e.g. EHR/EMR), may be difficult and fragmented. Typically, copies of medical data may be maintained at individual clinics, hospitals, laboratories or other locations remote to the patient/user. All of the foregoing, however, should report to the primary care physician. This is why access to the EHR/EMR of the primary care physician or hospital is a single source of the most comprehensive PHI. If a patient visits more than one clinic, for example, that patient may have a plurality of EHR/EMR. For example, the patient may visit a first clinic and create a first medical record and the patient may subsequently visit a second clinic and create a second medical record. If the second clinic does not have access to the first EHR/EMR, the examination and diagnosis at the second clinic may be duplicative and inefficient. An update of individual EHRs/EMRs does not ensure that each other copy is updated. Accordingly, the patient medical record information differs depending on the entity. Accordingly, it is difficult to locate a medical record that is completely up-to-date, and a treating physician may not be able to obtain a complete picture of a patient's health prior to treatment.

Moreover, this decentralized nature of patient EHRs/EMRs typically does not allow a patient to review a comprehensive report of his or her medical history and various conditions. The patient may not have the ability to access or update his or her medical records. In addition, the patient may not have the ability to restrict access to his or her medical records.

There are situations, such as may occur in a medical emergency, where a healthcare provider may need access to a particular patient's PHI. This is particularly true when a patient is outside of his/her locale and may not have direct or indirect access to his/her set of medical records (e.g. the patient is travelling). If there is a requirement for medical treatment or other medical service providers, it may be difficult to get access to the relevant EHR/EMR PHI. The problem of controlling, authorizing and authenticating access to relevant EHRs/EMRs presents significant challenges. EHR/EMR system administrators may allow certain providers access to a patient's PHI using a password/passphrase. Current EHR/EMR administrators require that healthcare providers be pre-authorized in order to view a patient's PHI in the EHR or EMR. Commonly, there may be no way for a health care provider to access the relevant PHI without such prior pre-authorization by the EHR/EMR administrator.

There is a need, therefore, for a system to allow healthcare providers and others to have immediate remote access to a patient's PHI without the forgoing having prior knowledge of who the provider is and without compromising the privacy and security of the patient's personal health information. Furthermore, there is a need to access the PHI of a particular patient residing in a plurality of unrelated EHR/EMR systems.

SUMMARY OF THE INVENTION

A broad aspect of the present invention is a method for allowing a remote user to have access to an electronic medical record of a patient stored on a first computer network, the method comprising: (a) the remote user requesting access to the electronic medical record from a second computer network and providing a first and second piece of patient derived information to the second computer network; (b) the second computer network transferring the first and second piece of patient derived information to a third computer network; (c) the third computer network authorizing the remote user through the first and second piece of patient derived information and dependent on a patient specific authorization protocol; (d) the third computer network confirming a patient specific consent protocol; and (e) the third computer network disclosing the electronic medical record to the remote user dependent upon an authorization received from the third computer network from step (c) and a confirmation received from the third computer network from step (d).

In a further embodiment, the patient specific authorization protocol is based on predetermined patient authorization criteria.

In yet a further embodiment, the patient authorization criteria is determined prior to step (a) above.

In yet a further embodiment, the predetermined patient authorization criteria is a patient specific identification number and a patient specific passphrase.

In yet a further embodiment, the patient specific consent protocol is based on predetermined patient consent criteria.

In yet a further embodiment, the predetermined patient consent criteria is determined by the patient prior to step (a).

In yet a further embodiment, the predetermined patient consent criteria is determined from a patient specific consent policy.

In yet a further embodiment, the method further comprising the step of providing at least one piece of remote user information to the second computer in step (a) and the step of the third computer network communicating with a fourth computer network to identify the remote user through the at least one piece of remote user information and dependent on a remote user identification protocol. In yet a further embodiment, the fourth computer network is a master provider registry. In yet a further embodiment, the master provider registry is the U.S. National Provider Identifier Registry or one of the Canadian College of Physicians & Surgeon Registries.

In yet a further embodiment, the remote user identification protocol is based on at least one predetermined user identification criteria.

In yet a further embodiment, the at least one piece of remote user information is determined prior to step (a).

In yet a further embodiment, the at least one piece of remote user information is selected from the group consisting of a user identification number, a user name and a user location.

A broad aspect of the present invention is a method for allowing a remote user to have access to an electronic medical record of a patient stored on a first computer network, the method comprising: (a) the remote user requesting access to the electronic medical record from a second computer network and providing at least one piece of remote user information to the second computer and at least one piece of patient derived information to the second computer; (b) the second computer network transferring the at least one piece of remote user information and the at least one piece of patient derived information to a third computer network; (c) the third computer network authenticating the remote user through the at least one piece of remote user derived information and dependent on a remote user specific authentication protocol; (d) the third computer network confirming a patient specific consent protocol based on at least one piece of patient derived information; and (e) the third computer network disclosing the electronic medical record to the remote user dependent upon an authentication received from step (c) and a confirmation received from the third computer network from step (d).

BRIEF DESCRIPTION OF THE DRAWINGS

The foregoing and other objects, features and advantages of the present invention should become apparent from the following description when taken in conjunction with the accompanying drawings.

FIG. 4 is a view of an embodiment of the present invention illustrating the initial selection by a remote user (e.g. a remote provider);

FIG. 6 is a view of an embodiment of the present invention directed to entering patient information; and FIG. 7; is a view of an embodiment of the present invention displaying a patient verification screen.

DESCRIPTION OF THE PREFERRED EMBODIMENTS

Figure 1:
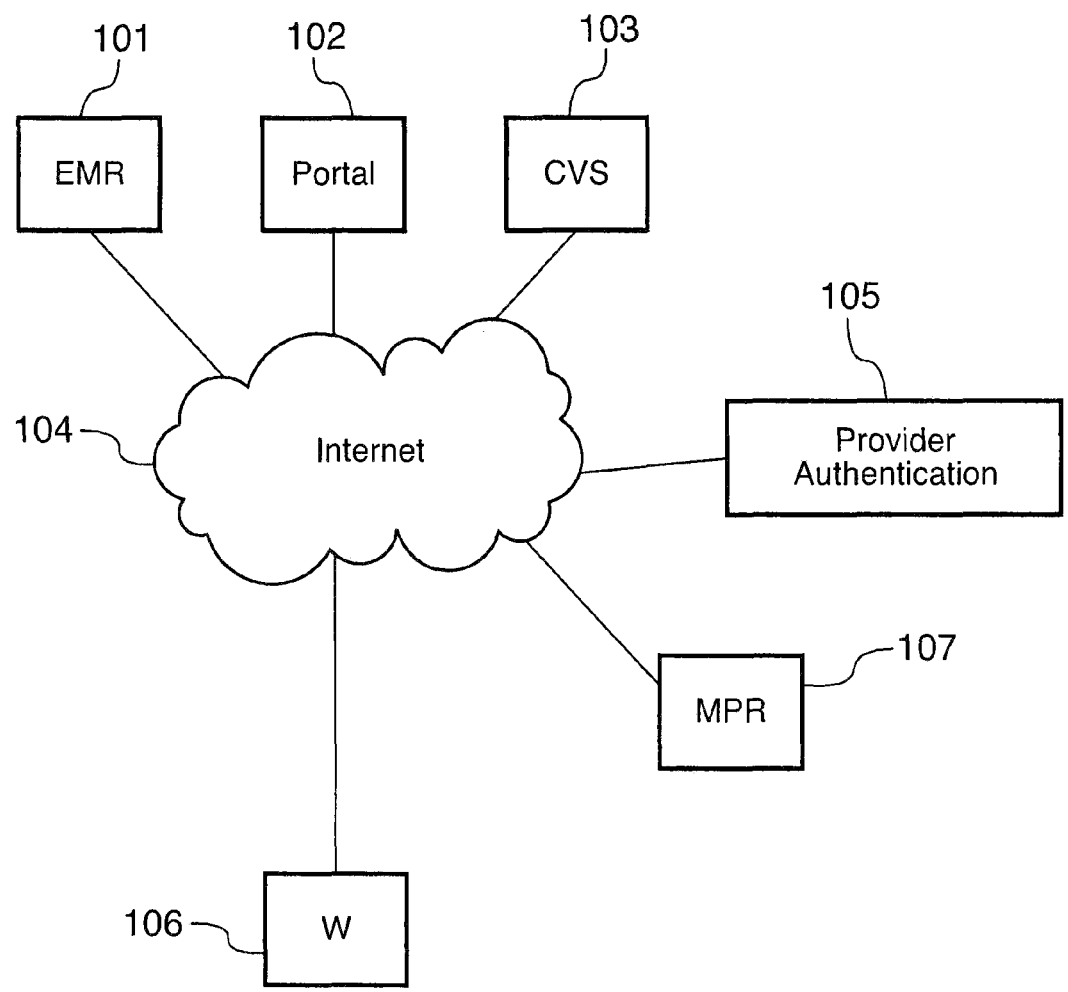
FIG. 1 is a view of an embodiment of the present invention directed to components of the remote emergency access system.

The description that follows, and the embodiments described therein, is provided by way of illustration of an example, or examples, of particular embodiments of the principles and aspects of the present invention. These examples are provided for the purposes of explanation, and not of limitation, of those principles and of the invention.

It will be understood by a person skilled in the relevant art that in different geographical regions and jurisdictions these terms and definitions used herein may be given different names, but relate to the same respective systems.

Although the present specification describes components and functions implemented in the embodiments with reference to standards and protocols known to a person skilled in the art, the present disclosure as well as the embodiments of the present invention are not limited to any specific standard or protocol. Each of the standards for Internet and other forms of computer network transmission (e.g., TCP/IP, UDP/IP, HTML, and HTTP) represent examples of the state of the art. Such standards are periodically superseded by faster or more efficient equivalents having essentially the same functions. Accordingly, replacement standards and protocols having the same functions are considered equivalents.

In the following specification, the terms "personal health information", "patient health information" "protected health information" or "PHI" will be used interchangeably and will be understood by a person skilled in the art to mean health information about or relating to a patient, including but not limited to, information relating to one or more of the following: (a) the physical or mental health of the individual, including information that consists of the health history of the individual's family; (b) the provision of health care to the individual, including the identification of a person as a provider of health care to the individual; (c) relates to payments or eligibility for health care, or eligibility for coverage for health care, in respect of the individual; and (d) a patient identification number.

In the following specification, the terms "remote access" and the like will be understood by a person skilled in the relevant art to refer to having access from a computer, network or system being remote from (e.g. any distance from) the location of another system (e.g. an EHR/EMR system) whereby the two systems are in communication via a data link (e.g. a network), which may be secure. Remote access is available by any number of secure data links, such as, for example, an internal network (intranet), an internet service provider (ISP), dial-up connection through desktop, notebook, or handheld computer modem over regular telephone line, or a dedicated line between a computer or a remote local area network and the "central" or main local area network. Remote access may also be used as part of a virtual private network (VPN). It will be further understood by a person skilled in the relevant art that a "remote user" is a user who has remote access.

In the following specification, the terms "electronic health records" or "EHR" will be understood by a person skilled in the art to refer to a collection of PHI in electronic or digital format that is capable of being shared across different health care information systems, by way of network-connected enterprise-wide information system and other information networks or exchanges. EHRs provide a range of data, including, but not limited to demographics, medical history, medication and allergies, immunization status, laboratory test results, radiology images, vital signs, personal stats like age and weight, and billing information.

In the following specification, the terms "electronic medical records" or "EMR" will be understood by a person skilled in the art to mean an electronic or digital medical record created or recorded in an organization (e.g. hospital, clinic, insurance provider, etc.) that contains EHRs.

In the following specification, the terms "master provider registry" or "MPR" will be understood by a person skilled in the art to mean any registry or directory that provides information of health care practitioners within a specific jurisdiction and used in the healthcare industry to provide electronic document submissions under applicable laws and regulations.

The invention broadly comprises a method and system for allowing patients, health care practitioners and others, including service providers, to have remote access to a patient's PHI through remote access to EHRs and/or EMRs. Embodiments of the present invention provide systems and methods for providing personalized, interconnected digital health services.

There are situations, such as may occur in a medical emergency, where a healthcare provider may need access to a particular patient's PHI without having had a prior relationship with the patient and therefore the provider/patient information access policy will not be known to the applicable systems that authenticates and/or authorizes access to the patient's PHI. In other words, it may be required in such circumstances that a user (e.g. a health care provider) requires access to the applicable EHR/EMR without prior authorization and/or prior authentication by the patient or others. This is particularly true when a patient is outside of his/her locale and may not have direct or indirect access to his/her set of medical records (e.g. the patient is travelling). If there is a requirement for medical treatment or other medical service providers, it may be difficult to get access to these electronic medical records.

The present invention is directed to a remote electronic medical record access service (REMRAS) and/or system that is operably connected to the applicable networks or systems (e.g. EHR or EMR systems, CVS, MPR, provider identification/authentication services, etc.). EHR or EMR systems are well known to a person skilled in the art and typically comprises an on-line system that holds the relevant EHR/EMR of a patient. The REMRAS of the present invention may also be operably connected to a provider identification services, such as, a master provider registry (MPR), which may comprise a central and authoritative source of listed healthcare providers or practitioners, including where they work and how to be contacted, typically an on-line system, which can also be used to provide information on users. The REMRAS of the present invention may also be operably connected to a provider authentication services, such as, Equifax/Anakam, Auththentify or Resilient Networks, which may comprise a central and authoritative source of healthcare provider information that can be used to authenticate the identified remote user or remote provider. Finally, the REMRAS of the present invention may also be operably connected to a consent management and/or validation service (CVS) which may further contain patient derived authorization criteria.

FIG. 1 is a block diagram of an embodiment of the present invention 100 for allowing remote access to patient data, including, but not limited to, electronic health records. The embodiment of the present invention as shown in FIG. 1 is made up of the several components operably connected or otherwise linked by means of a computer network 104, including, but not limited to, the Internet. As shown in FIG. 1, there is provided an Electronic Medical Record (EMR) system 101 that contains protected health information (PHI) of the patient, such as will be familiar and/or required by those practicing or providing services in the medical field, such as, for example, healthcare practitioners/providers and insurance providers. As shown in FIG. 1, there is also provided a portal component 102 and a consent management/validation service (CVS) component 103. The embodiment of the present invention shown in FIG. 1 may also include a service or system 107 (e.g. master provider registry (MPR)) communicating over the network 104 and a workstation or similar computer 106, that is used by or otherwise associated with a healthcare provider and is operatively connected to the network 104 (e.g. able to download software, such as, for example, applications and access web pages) and a Provider Authentication Service 105 used to authenticate a remote user (e.g. a remote provider). Each of these components will be discussed in greater detail below.

Figure 2:
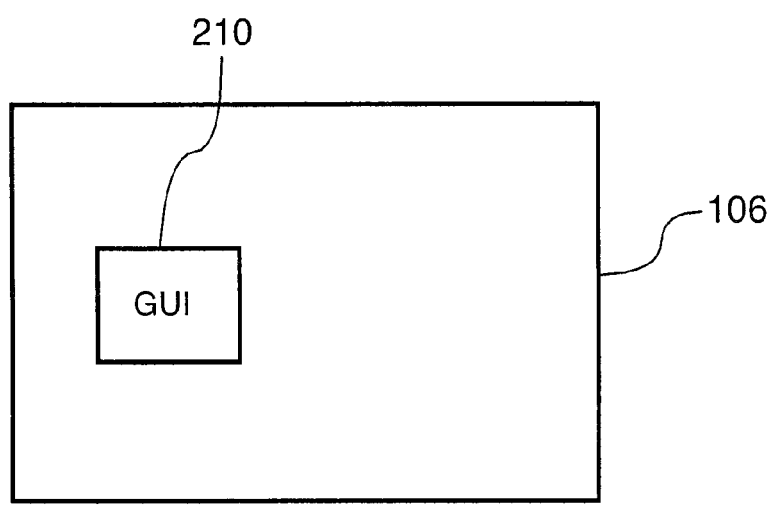
FIG. 2 is a view of an embodiment of the present invention directed to a health care provider computer.

As shown in FIG. 2, the workstation 106 may comprise interface element 210 and other functional elements required for the workstation that would be understood by a person skilled in the relevant art, including those of at least one specially programmed general-purpose computer. It will be understood that interface element 210 may comprise a graphical user interface (GUI) as a human-computer interface (i.e., a way for humans to interact with computers) that uses windows, icons and menus and which can be manipulated by a mouse (and often to a limited extent by a keyboard as well). The interface element is for receiving data regarding at least one environmental condition related to the patient, including but not limited to at least one symptom related to physical or mental health of the patient and background data of the patient. In a preferred embodiment, interface element 210 may comprise a web browser or a browser.

Remote user (e.g. health care provider) information can be used to identify a remote user and assert identification, authentication and/or authorization. By means of these applicable health care provider credentials and subsequent identification, authentication, and/or authorization, remote users, including but not limited to remote providers, may be granted access to the patient's EMR or EHR system. Final authorization of a remote provider for access to PHI in an EMR or EHR may also require the use of a consent validation service (CVS).

In accordance with the embodiment of the present invention, there is provided a consent management service that enables EMR administrators to create and administer patient specific privacy PHI disclosure rules and a password or passphrase on behalf of the patient. In a preferred embodiment, a patient can be advised that his/her PHI is private and is to be held in confidence by healthcare providers/Care Delivery Organizations (CDOs) subject to permitted disclosures by the organizations who maintain it. The patient is further advised that these organizations may have privacy obligations regarding disclosure (sharing) of PHI. As adjudicated by the CVS, the PHI may be disclosed with the patient's explicit consent and only through the practices of the present invention. In a preferred embodiment, the patient (or someone designated thereby) must provide a piece of information that can identify that patient specifically (e.g. a personal passphrase). Accordingly, PHI disclosure can then be made to any other party knowing this passphrase. If the patient is unable to provide the applicable passphrase, disclosure will only be to an authenticated healthcare provider. Also, the patient may further restrict disclosure in greater detail (e.g. Emergency departments only). These consent directives may be subsequently changed by the patient by accessing a patient specific portal. Once the access rules, have been created from the consent directive(s), a consent validation service (CVS) applies these rules thereby adjudicating appropriate disclosure of the relevant PHI.

By providing both the patient ID number and the secret Passphrase known only to the patient (and his/her designate), the patient is personally authorizing and authenticating anyone he/she chooses worldwide to have access to the patient's PHI, regardless of who or where the individual is located. Should the patient not remember his/her passphrase, or be unable (e.g. is unconscious) to provide his/her passphrase, then access to PHI may be granted through an external pre-certified service (as may be available where he/she is at the time) that authenticates the individual as that specific remote user (e.g. healthcare provider).

In a preferred embodiment, the patient can further predetermine the department(s) (e.g. Emergency Department only), State(s)/Province(s) and Countries any remote user must be in to have access. This is accomplished through choosing to update the patient's consent policy. Subsequently, if any one of these attributes does not match the allowances in the patient derived consent policy then the remote user will not be allowed access. For situations should he/she not be able to provide their Passphrase and should the Provider Authentication Service 105 (e.g. Equifax/Anakam, Auththentify, Resilient Networks, etc.) not be able to authenticate the Healthcare Provider, it is recommended that the patient has given his/her passphrase to a designated emergency contact designated on the back of the patient's wallet card to be contacted.

In an alternate embodiment, access to the EMR may be provided using a pool of credentials. The credentials of the EMR may be provisioned specifically for this purpose such that a number of different log-in accounts are available for use. Hence each time access is provided for a new healthcare provider, a different EMR user account may be used. This may allow the actions of the provider to be correctly logged by the EMR and permits the REMRAS portal 102 to disambiguate one provider from the actions of another provider accessing the EMR under similar conditions.

In a preferred embodiment, once the web portal has been accessed, a provider can be identified, authenticated, and/or authorized. In computer networks, such as, for example, internet 104, these steps are commonly done through the use of remote user and/or patient derived information. In a preferred embodiment, knowledge of the patient derived passphrase by the remote user is assumed to guarantee that the user is both authentic and authorized.

For identification and/or authentication purposes, each user (e.g. a health care provider) registers initially (or is registered by someone else), using user specific information (e.g. an assigned or self-declared password). On each subsequent use, the remote user must know and use the previously identified user specific information. Healthcare providers must typically be registered, and therefore known, to each particular electronic records system in which the EHR/EMR is stored and maintained. When greater security is required, transactions require a more stringent authentication process. The use of digital certificates issued and verified by a Certificate Authority (CA) as part of a public key infrastructure is considered likely to become the standard way to perform authentication on the internet. Once registered, each healthcare provider will be issued credentials that identify them to the applicable EHR/EMR system. While this system may be secure, it may not easily allow access for each health care provider to each electronic records system in which the EHRs/EMRs are provided (e.g. EHR/EMR systems). An aspect of the present invention is to include an access portal providing access to a patient's PHI in a plurality of data sources (i.e. applicable EHR/EMR systems) regardless of whether or not the health care provider has been registered with a specific EHR/EMR system.

In a preferred embodiment of the invention, authentication may also include authorization. As noted previously, if the remote user has the necessary patient derived information (i.e. patient ID and passphrase), the remote user may be both authenticated and authorized.

Figure 3:
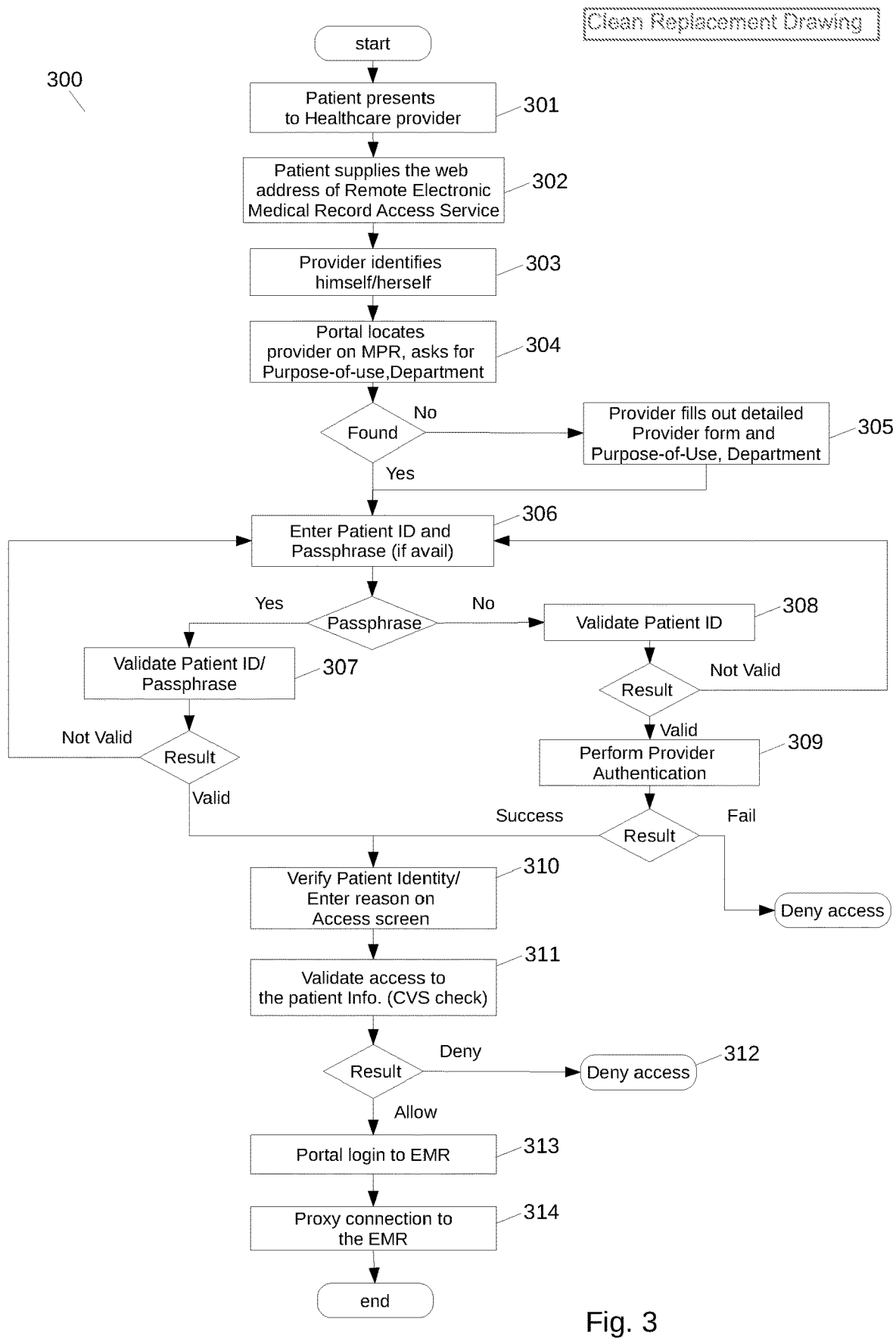
FIG. 3 is a flow chart that schematically illustrates a method for remote access, in accordance with an embodiment of the present invention.

FIG. 3 is a flow chart that schematically illustrates remote access method 300 described herein in accordance with the operation of an embodiment of the present invention. The method 300 begins at 301 where, as the result of an unexpected medical occurrence, for example, an accident in a foreign location, a patient may present to a healthcare provider (e.g. provider A), whom the patient has not seen before. During this consultation, provider A examines the patient and then requests access to the patient's medical history, which may be located or otherwise stored on a remote EHR/EMR system (e.g. the EMR system of the patient's healthcare provider). This patient's PHI may be required in order to provide the best treatment for the patient. In order to provide provider A with access to the PHI contained within the applicable EMR system, provider A must obtain the necessary or applicable access details, typically from the patient directly, in order to interoperate with the applicable EMR system (see 302). It will be understood by a person skilled in the relevant art that provider A may contact the applicable EMR system through any networked workstation (e.g. workstation 106).

When provider A requires accessing the patient's PHI, he or she will use the interface 210 (e.g. a web browser) on the networked workstation to access a web portal 102 at the internet address provided by the patient (see 302 of FIG. 3). Web portal 102 with which the patient is associated may be in the form of a web-based browser application or an application downloaded from the network 104. In a preferred embodiment, this web portal address may be printed on a wallet-card carried by the patient. In further preferred embodiments, the web portal information may be provided on a magnetic-stripe card, an optical barcode or 2-D optical code, a USB memory stick or other such portable electronic media. In a preferred embodiment, access to the EMR will be provided using web portal 102 as a proxy server. Because the Provider may not be known (i.e. neither authenticated nor authorized) to the EMR, the EMR login may be using specific user credentials for the EMR prearranged for use by the portal 102. Access may be therefore restricted to those EMR functions allowed by the EMR. For example, the EMR may define access using this method to be 'read only'.

Figure 5:
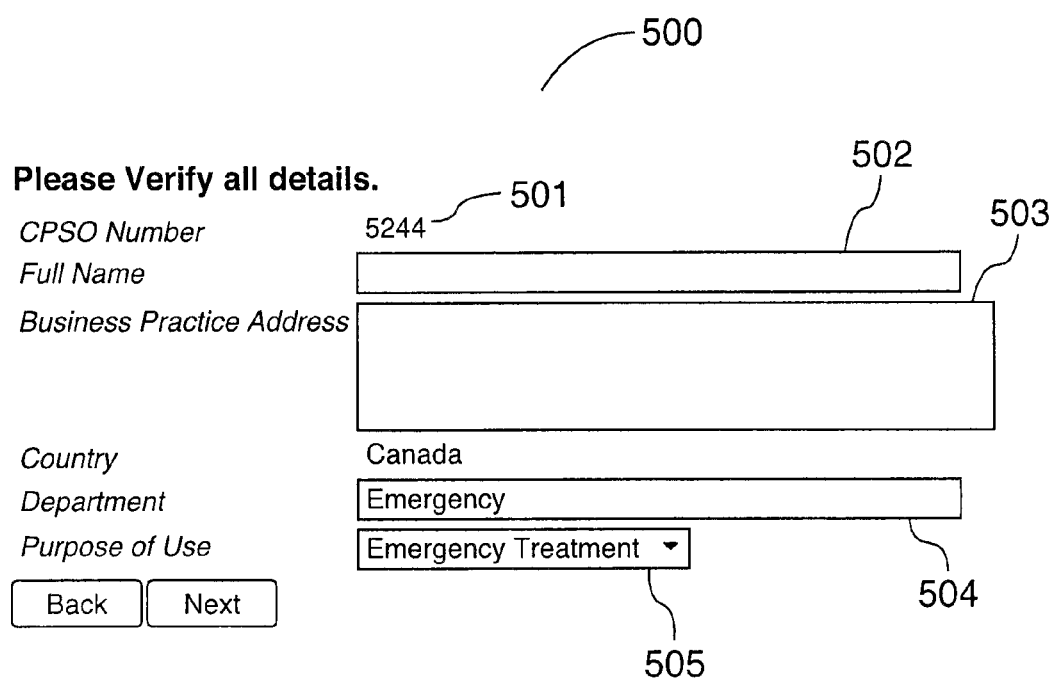
FIG. 5 is a view of an embodiment of the present invention directed to entering remote user information.

Once logged on, the remote provider will provide information to the web portal that will identify that provider (see 303 in FIG. 3). Whether combined with this step or as a later step, the remote provider may also provide patient specific information (e.g. patient ID and patient passphrase/password). As shown in FIG. 3, 303 requires the provider to provide identifying information. This is shown in greater detail in FIG. 4. The first screen 400 presented to provider A will allow him (or her) to select the country of registration 401 as shown in FIG. 4. As can be seen in FIG. 4, a number of options may be available for the health care provider to select and identify the relevant identifying information of provider A. Once the appropriate information has been selected, provider A will be directed to a following input screen 500 (see FIG. 5) in which additional information must be provided before provider A can continue. Once the information is provided, the portal will locate the provider within a master provider registry (MPR) (see 107 in FIG. 1) and attempt to locate applicable provider details (see 304 in FIG. 3). As shown in FIG. 5, provider A may be required to provide one or more of the following in 303: (a) provider identifier 501; (b) provider name 502; (c) business practice location address 503. Following entry of any applicable information of the health care provider by the provider or others (e.g. provider A identifier number), the web portal 102 may access MPR 107 and attempt to locate additional provider details, including the Business Practice address. The REMRAS may use the information entered by Provider A to bring up the provider demographics (e.g. information related or specific to that provider) using the MPR, such as, for example, the U.S. National Provider Identifier (NPI) Registry. As another example, in Canada, the provincial College of Physicians and Surgeons provides for a Provincial registry. A search under a CPSO (College of Physicians and Surgeons of Ontario) number as in FIG. 5. 501 is a preferred embodiment. In a more preferred embodiment, the NPI Registry enables users of the present invention, including both individuals and computer systems, to search for a health care provider's information, such as NPPES information. For example, users may search for a provider by the NPI or Legal Business Name. Some health care providers provide their SSNs, IRS ITINs or EINs in sections of the NPI application that contain information that is required to be disclosed under applicable legislation. For example, Providers who are individuals may have reported SSNs or IRS ITINs in FOIA-disclosable fields (such as in the "Other Provider Identifiers" or "License Number" fields). An incorporated individual, when applying for an NPI for the corporation, may have reported his/her SSN as the EIN of the corporation.

MPR-provided fields (including, but not limited to, 'Name', 'Provider ID', 'Business Practice Location Address') as well as the 'country' as identified by Provider A and 'department' as entered by Provider A may be captured by the system of the present invention and may be stored therein in either short term or long term memory. Once the applicable information has been found in the MPR, the details of provider A can be displayed on the screen and the Provider can be asked to confirm that they are correct. If the applicable information has not been found in the MPR (503 of FIG. 5), the provider may enter these fields manually (305 of FIG. 3). Once the applicable information has been found in the MPR or manually entered and is identified as correct, the purpose of use can be identified or entered (see 505) along with the provider's department 504. Provider A may have to explicitly affirm the purpose-of-use for which the access is required, such as for 'Emergency Treatment' and for this purpose a data entry field may be presented to the Provider A. Once the information is provided, the health care worker can click "Next" as shown in FIG. 5 to proceed to the next screen.

It will be obvious that the same approach may be taken for Purposes-of-Use other than Emergency Treatment, such as consultation with additional providers, among others. An example may be an EMR Administrator providing the EMR Patient ID and a passphrase to the consultant as information entered by the provider. Similarly, the patient him/herself may use the service to access their PHI.

Once the provider information has been entered or retrieved, as applicable, the identified remote user can then be authenticated and authorized. This comprises at least two steps. Web portal 102 can request that the remote user provide one or more patient specific data, such as, but not limited to a patient ID, a password, or other identifying data (306 of FIG. 3). The request for the patient specific data allows for the remote user to be authenticated and authorized. If the remote user has both the patient ID and passphrase, for example, then the remote user can enter the passphrase into the web portal at which point the passphrase can be validated and it can be determined whether the remote user can be authorized (see 307 of FIG. 3). Resulting from this authorization will be either (a) an 'Allow' response to allow access to the patient's PHI or (b) a 'Deny' response to indicate that the information parameters presented are not sufficient to allow the remote user (e.g. remote provider) to access the patient's PHI. If the passphrase is correct, remote user may be required to enter the purpose of use/reason for access (see 310 of FIG. 3). In this embodiment, the system confirms (see 311 and 312 of FIG. 3) that a consent policy has been created by the patient (as noted herein). If such a consent policy exists, then the web portal 102 accesses the EMR by establishing a proxy connection to the EMR (see 313 and 314 of FIG. 3). At this point, the remote user will have access to the EMR. Upon receipt of the 'Allow' response from the CVS, the REMRAS will proxy the Provider's interface to the EHR/EMR service, where the Provider will be logged in using REMRAS credentials. This allows the authorized/authenticated Provider to view the patient's PHI to the extent predetermined by the EHR/EMR.

In a preferred embodiment, it will be understood by a person skilled in the relevant art that the remote user may be the patient, a health care provider, an administrator or any one else authenticated and authorised by the owner of the PHI contained in the EMR. By having the patient specific information (e.g. patient ID and passphrase), the remote user has been both authenticated and authorized.

In another embodiment of the present invention, the remote user may not have all the necessary information required to be both authenticated and authorized. If the remote user believes that he/she must have access to the patient's information, such as may occur when the patient is not able to provide a password/passphrase or to provide the correct password/passphrase, then the REMRAS may invoke a further embodiment to authenticate the provider's identity in cases where such authentication is available. Such a provider authentication service may be supplied by a $3^{rd}$ party using messaging over the Internet (e.g. Equifax/Anakam, Auththentify or Resilient Networks, etc.). In such cases, separate authentication and authorization steps may be required. In this embodiment, the remote user (e.g. provider A) may only have the patient TD, which is then entered into web portal 102 and validated as being correct (see 308 of FIG. 3). If the patient ID is correct, the remote user must be authenticated (e.g. identified as the remote user provided in 304). During this authentication step 309, additional remote user specific information will be requested which will require the remote user to confirm that he/she is the person so identified in 304/305. If this authentication step fails (e.g. the remote user is unable to provide the information requested and/or required), then authorization is denied and the remote user is not granted access to the applicable EMR. If this authentication step succeeds (e.g. the remote user is able to provide the information requested and/or required), then authorization is affirmed and the web portal proceeds to 310 of the process seen on FIG. 3. The CVS check then confirms that (a) a consent policy exists; and (2) that the remote user's access to the EMR is under circumstances that are permitted according to the patients pre-filled consent management policy/directives in accordance with the subsequent rules adjudicated in the CVS.

Consent management/validation is a process that includes: (1) enabling patients to establish privacy preferences/policies to direct who shall have access to their electronic PHI, for what purpose and under what circumstances; and (2) supporting the dynamic creation, management and subsequent enforcement of consumer's/patient's, privacy policies through access control mechanisms. Consent validation occurs after consent and privacy policies have been created and stored as consent validation/adjudication rules. This may be provided within the web portal (e.g. as a component of the software) or within an external system as a service. CVS is accessed using a secure Internet protocol for final determination if access to the patients PHI is permitted. In a preferred embodiment the OASIS XACML protocol may be used, but it should be understood that other access request protocols may also be employed. In one embodiment, an embodiment of the present invention may also require the selection or insertion of a PHI Purpose-of-use as a required CVS attribute for validation. In all cases an access screen 700 will be presented to the Provider (see FIG. 7) to verify the patient's identity and insert the access reason as the final step required to complete CVS validation. Once all requirements are met for CVS validation, he/she is connected to the EMR via a proxy server, preferably through the web portal 102. Access acceptance may cause an alert message to be sent to the Privacy Officer address designated for the EMR. It may also cause an alert message to be sent to the notification address previously provided by the patient. Said messages may be of the form of one or more of an e-mail, text message, voice message, telephone notification or another form.

The lack of harmonized requirements across various jurisdictions does not permit a detailed uniform consent model. However, by using the patient directed consent management service, it is possible to develop a set of rules to deal with consent, PHI disclosure, auditing, and other privacy code principles. Consent will apply to the stated purpose for disclosure of personal information and may apply as narrowly or as broadly as the patient directed consent policies allow. After provision of provider A's information in 503, the next step may be for Provider A to enter the desired parameters such as the EMR system's patient ID and the patient password, passphrase or key. Patient ID 601 and passphrase 602 will be requested in screen 600 (see FIG. 6). Both of these may be obtained from the patient directly by Provider A. The patient may, for example, carry a wallet-card to provide the REMRAS URL and the EMR patient ID for this purpose. The password or passphrase may come from the patient's or a third party's memory. In a preferred embodiment, there may be more patient credentials required, such as the answer to a challenge question, or some other well known authorization method using a secret known only to the patient. If the patient desires more confidentiality, the patient may enter the password or passphrase directly on the Provider A's computer without divulging it to Provider A. The EMR patient ID and the password/passphrase may be validated before proceeding. This validation in itself does not constitute an EMR sign in operation. CVS validation is an additional requirement prior to sign in to view the patient's PHI.

Following the parameter or parameters entry, the REMRAS will authorize access to the patient's PHI by the provider by querying the consent validation service (CVS) which may be over the Internet in a manner that is well known (See 104 of FIG. 1). As part of a CVS validation, an access screen may appear in which Provider A must provide additional details as to the reason to have PHI access (See 700 in FIG. 7). The information provided by Provider A will be used to create an audit trail of the access and may be used as attributes for CVS validation. In a preferred embodiment, it may also cause a message, such as an e-mail or text message, to be sent to a designated individual (e.g. a privacy officer) to alert one or more of the PHI access. In a further preferred embodiment, it may also cause a message, such as an e-mail message or a text message to be sent to one or more destinations provided by the said patient to alert the patient to emergency or other access to the patient's PHI.

While preferred aspects of the present invention have been described in detail, various modifications, alterations, and changes may be made without departing from the spirit and scope of the present invention as defined in the appended claims.

We claim:

1. A method for allowing a provider who has not been registered with a first electronic medical record (EMR) computer network to have access to an EMR of a patient stored on the first EMR computer network, the method comprising:
    (a) the patient presenting to the provider and identifying to the provider a second computer network to authenticate and authorize the provider to allow provider access to the electronic medical record, the second computer network separate from the first EMR computer network;
    (b) the second computer network receiving from the provider a provider information and a practice location and the second computer network locating and identifying the provider on a master provider registry separate from the first and second computer networks based on the provider information and the practice location;
    (c) the second computer network receiving from the provider, a request for access to the electronic medical record and the provider providing to the second computer network a patient ID;
    (d) the second computer network validating the patient ID and authenticating the provider based on the provider information to authenticate the provider independently of the first EMR computer network;
    (e) the second computer network confirming the existence of a patient specific consent protocol with a consent validation service and confirming whether the electronic medical record can be accessed by the provider based on:
        (i) the second computer network presenting to the provider a list of purposes of use for accessing the EMR and the provider having explicitly affirmed an affirmed purpose of use;
        (ii) the provider having explicitly entered an affirmed reason for access;
        (iii) comparing the affirmed purpose of use with a purpose of use established in the patient specific consent protocol with the consent validation service and validating the affirmed reason for access with a reason for access established in the patient specific consent protocol with the consent validation service; and
        (iv) where the affirmed purpose of use and the affirmed reason for access each match the allowances in the patient derived consent policy; and
    (f) the second computer network establishing a proxy connection to the first EMR computer network for access to the electronic medical record for the provider in response to steps (d) and (e).

2. The method of claim 1, wherein step (b) is dependent on a provider specific identification service.

3. The method of claim 1, wherein step (d) comprises authenticating the provider from a provider authentication service.

4. The method of claim 1, wherein the patient specific consent protocol is based on a patient consent policy.

5. The method of claim 4, wherein the patient consent policy is determined by the patient prior to receiving the request for requesting access from the provider.

6. The method of claim 5, wherein the patient consent policy identifies circumstances under which the provider is permitted access to the electronic medical record.

7. The method of claim 3, wherein the provider specific authentication service is a central source of healthcare provider information.

8. The method of claim 7, wherein the central source of healthcare provider information is a master provider registry.

9. The method of claim 7, wherein the master provider registry is selected from a group consisting of the U.S. National Provider Identifier Registry and one of the Canadian College of Physicians Surgeon Registries.

10. The method of claim 1, wherein the patient's identity is verified between steps (d) and (e).

* * * * *